US00PP33523P2

(12) United States Plant Patent
Van Swieten

(10) Patent No.: US PP33,523 P2
(45) Date of Patent: Sep. 28, 2021

(54) ***PHALAENOPSIS* ORCHID PLANT NAMED 'PHALIDDIK'**

(50) Latin Name: ***Phalaenopsis* hybrid**
Varietal Denomination: PHALIDDIK

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,219

(22) Filed: Apr. 15, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

Pluto Database UPOV hit on *Phalaenopsis* plant named 'PHALIDDIK', QZ PBR 2019/2362, Sep. 23, 2019.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALIDDIK', particularly characterized by light greenish-yellow, flecked flowers with light greenish-yellow and white lips, flowers with a flat shape in lateral view, apical lobes of the lip with a small bump and ridge, and is propagated by meristem tissue culture, is disclosed.

3 Drawing Sheets

Genus and species: *Phalaenopsis* hybrid.
Variety denomination: 'PHALIDDIK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALIDDIK'.

The new *Phalaenopsis* plant is a product of a planned breeding program conducted by the inventor in Bleiswijk, the Netherlands. The objective of this breeding program was to create a new *Phalaenopsis* plant with small, light greenish-yellow, flecked flowers with light greenish-yellow and white lips, suitable for potted plant production.

The new *Phalaenopsis* plant 'PHALIDDIK' is a result of cross-pollination made by the inventor in February 2012 in Bleiswijk, the Netherlands, of the proprietary female, or seed parent, *Phalaenopsis* hybrid '01-4155' (unpatented) with the proprietary male, or pollen parent, *Phalaenopsis* hybrid '01-3358' (unpatented).

The new *Phalaenopsis* was selected by the inventor as a single plant within the progeny of the stated cross-pollination in a controlled greenhouse in Bleiswijk, the Netherlands, in January 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 23, 2019 (Application no. 2019/2362), by Applicant who obtained the subject matter disclosed directly from the inventor. 'PHALIDDIK' has not been made publicly available or sold anywhere in the world prior to the effective filing date of this application with the exception of sales or disclosures made one year or less before the effective filing date of this claimed invention by Applicant who obtained 'PHALIDDIK' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALIDDIK' as a new and distinct variety of *Phalaenopsis* plant:

1) Light greenish-yellow, flecked flowers with light greenish-yellow and white lips (intensity and number of flecks depend on temperature during growing period);
2) Flower shape in lateral view is flat; and
3) Apical lobe of the lip has a small bump and ridge.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2021. Colors in the photographs may differ from the color values cited in the detailed botanical description, which accurately describe the actual colors of the new variety.

DESCRIPTION OF THE NEW VARIETY

Figure 1:
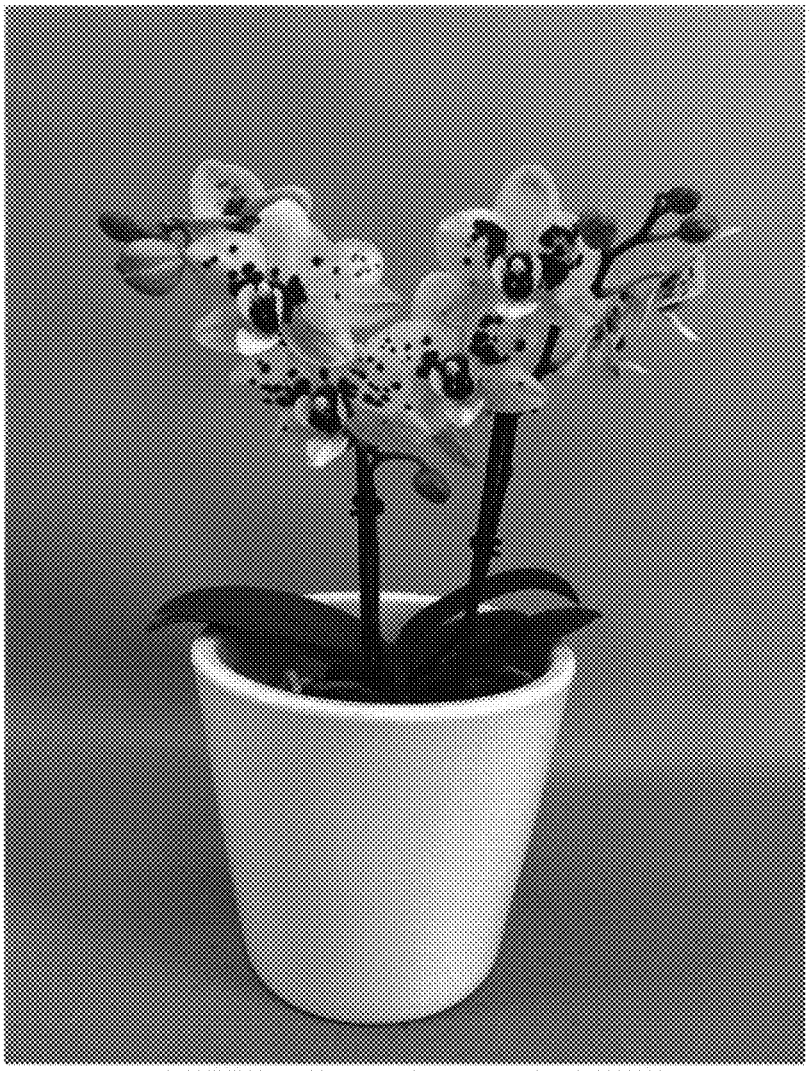
FIG. 1 shows the overall plant habit, including blooms, buds, and foliage of 'PHALIDDIK'.
Figure 2:
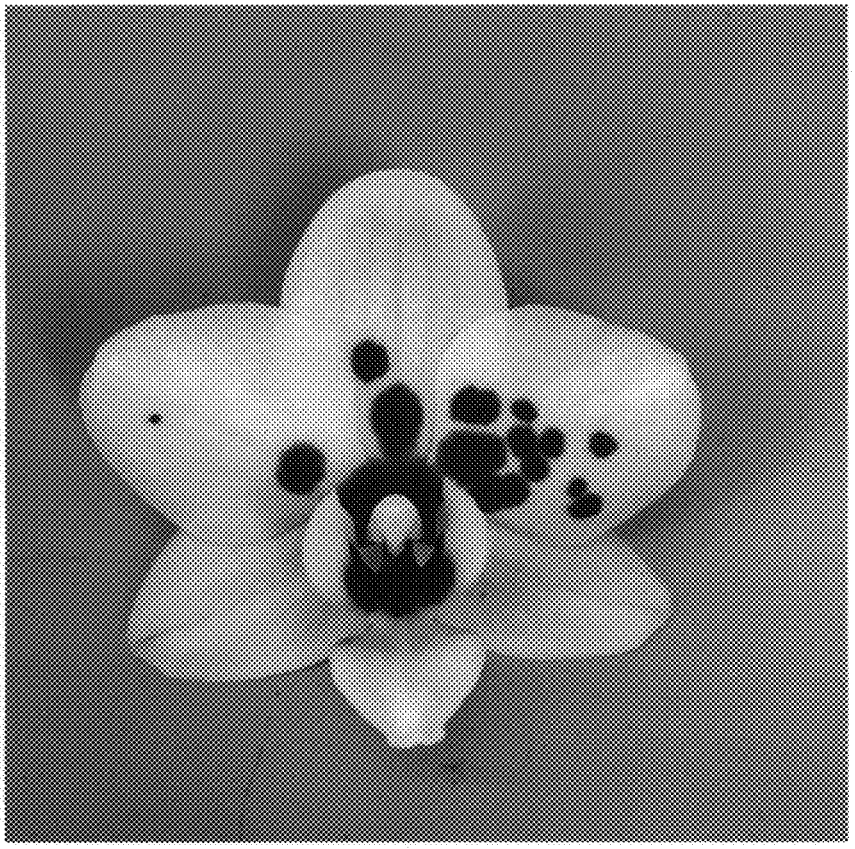
FIG. 2 shows a close-up of a flower of 'PHALIDDIK'.
Figure 3:
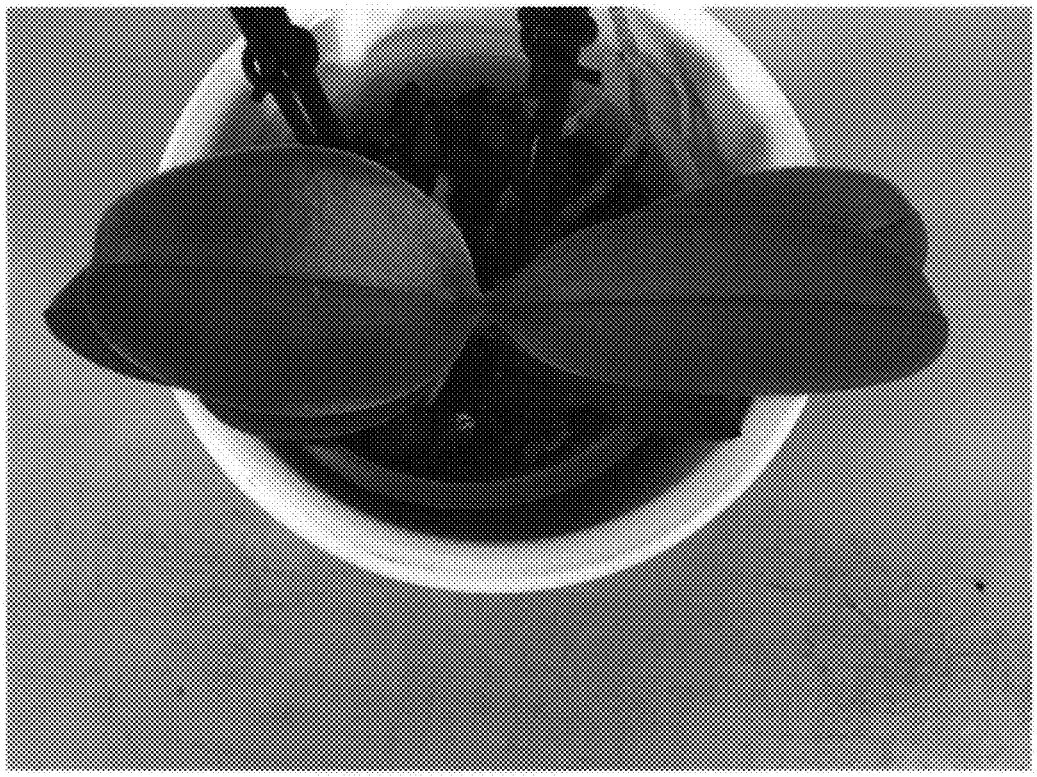
FIG. 3 shows an overhead view of the leaves of 'PHALIDDIK'.

The following detailed description sets forth the distinctive characteristics of 'PHALIDDIK'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALIDDIK'.

Parentage:

*Female parent*.—*Phalaenopsis* cultivar '01-4155' (unpatented).

*Male parent*.—*Phalaenopsis* cultivar '01-3358' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 145A) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height (from soil level to top of inflorescence)*.—Approximately 18.0 cm to 23.0 cm.

*Width (measured from leaf tips)*.—About 19.0 cm to 21.0 cm.

*Vigor*.—Strong.

Leaves:

*Mature leaves*.—Quantity per plant: 7 to 8 leaves are produced before flowering. Length (fully expanded): 9.0 cm to 11.0 cm. Width: 5.0 cm to 6.0 cm. Position of the broadest part of the leaf: At the middle. Shape: Oblong. Base shape: Moderately to slightly elongated. Apex: Unequal obtuse. Leaf blade angle with the petiole (measured from the horizontal position): Between 15 degrees and 35 degrees. Leaf margin: Entire. Color: Upper surface: Yellow-green (RHS 146A) and dark red (RHS 187B). Lower surface: Yellow-green (RHS 146B) and diluting dark red (a color in between RHS 187B and RHS 187C). Texture (both upper and lower surfaces): Smooth. Thickness: 2.0 mm to 3.0 mm. Variegation: Absent. Venation: Pattern: Parallel. Color of the midvein: Upper surface: Dark red (RHS 187B). Lower surface: Dark red (a color in between RHS 187B and RHS 187C) with a touch of yellow-green (RHS 146C).

Peduncle:

*Quantity per plant*.—1 to 2.

*Number of flowers per peduncle*.—8 to 12.

*Length*.—19.0 cm to 21.0 cm.

*Diameter*.—2.7 mm to 3.2 mm.

*Strength*.—Strong.

*Aspect*.—Upright to slightly pendent.

*Texture*.—Smooth.

*Color*.—Dark reddish-brown (a color in between RHS 187A and RHS 200B) with a touch of yellow-green (RHS 146C).

*Internode length*.—2.0 cm to 3.0 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 90.0 mm to 120.0 mm.

*Flowering time*.—First flowers can be expected 10 to 11 months after planting in a 12-cm pot.

*Flower*.—Height: 50.0 mm to 55.0 mm. Diameter: 55.0 mm to 60.0 mm. Depth of lip: 15.0 mm to 17.0 mm.

*Flower longevity*.—On the plant: 16 to 18 weeks.

*Flower shape*.—Flat.

*Fragrance*.—Absent.

*Flower bud*.—Average size: Medium. Length: 17.0 mm to 19.0 mm. Width: 13.0 mm to 15.0 mm. Shape: Egg shaped. Color: Diluting dark purplish-red flecks (RHS N79A) at the base; yellow-green (RHS N144D) with a touch of dark purplish-red (a color in between RHS N79B and RHS N79C) toward the tip.

*Petals*.—Arrangement: Open/free. Shape: Semi-circular. Apex: Emarginated asymmetric. Margin: Weakly undulated. Length (from base to tip): 24.0 mm to 26.0 mm. Width: 24.0 mm to 26.0 mm. Position of the broadest part of the petal: Toward the base. Color (when fully opened): Upper surface: Basic color: Light yellow-green (RHS 2C). Over color: Dark red-purple flecks (a color in between RHS 187B and RHS N79C). Lower surface: Basic color: Light greenish-yellow (RHS 2C). Over color: Diluting dark red-purple flecks (a color in between RHS 187B and RHS N79B). Number of spots, flecks, and stripes on the petals (upper surface): Medium flecks.

Color of spots, flecks, and stripes on the petals (upper surface): A color in between RHS 187B and RHS N79C. Density of netting of the petals (upper surface): None. Color of the netting (upper surface): Not applicable.

*Dorsal sepal*.—Shape: Elliptic. Apex: Rounded symmetric. Margin: Entire. Length (from base to tip): 24.0 mm to 26.0 mm. Width: 18.0 mm to 20.0 mm. Position of the broadest part of the dorsal sepals: At the middle. Color (when fully opened): Upper surface: Basic color: Yellow-green (RHS 154C). Over color: Dark purplish-red base and flecks (RHS N79C). Lower surface: Basic color: Yellow-green (RHS 154C). Over color: Diluting dark purplish-red flecks (RHS N79B). Number of spots, flecks, and stripes on the dorsal sepals (upper surface): Very few flecks. Color of spots, flecks, and stripes on the dorsal sepals (upper surface): RHS N79C. Density of netting of the dorsal sepals (upper surface): None. Color of the netting: Not applicable.

*Lateral sepals*.—Shape: Ovate. Apex: Obtuse symmetric. Margin: Entire. Length (from base to tip): 26.0 mm to 28.0 mm. Width: 17.0 mm to 19.0 mm. Position of the broadest part of the lateral sepals: At the base. Color (when fully opened): Upper surface: Basic color: Light yellow-green (RHS 2C). Over color: Dark red-purple flecks (a color in between RHS 187B and RHS N79C) and light yellow-green (RHS 145D) at the middle. Lower surface: Basic color: Yellow-green (RHS 154C). Over color: Diluting dark red-purple flecks (a color in between RHS 187B and RHS N79B) and purplish-red midvein (RHS N77B) toward the tip. Number of spots, flecks, and stripes on the lateral sepals (upper surface): Few flecks. Color of spots, flecks, and stripes on the lateral sepals (upper surface): A color in between RHS 187B and RHS N79C). Density of netting of the lateral sepals (upper surface): None. Color of the netting (upper surface): Not applicable.

*Labellum* (*lip*).—Whiskers: Present, but very short. Length of whiskers: 1.0 mm to 2.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 14.0 mm to 16.0 mm. Width: 7.0 mm to 9.0 mm. Color: Upper surface: Dark red fleck (a color in between RHS 187A and RHS 187B) at the base; greenish-yellow margin (RHS 6B) on one side; white (RHS NN155C) toward other side and tip. Lower surface: Diluting dark red (a color in between RHS 187A and RHS 187B) at the base; greenish-yellow margin (RHS 6C) on one side; white (RHS NN155C) toward the other side and tip. Number of spots, flecks, and stripes on the lateral lobe: One large fleck. Color of spots, flecks, and stripes on the lateral lobe: A color in between RHS 187A and RHS 187B. Density of netting of the lateral lobe: None. Color of the netting: Not applicable.

*Apical lobe*.—Shape: Ovate. Margin: Entire. Length: 15.0 mm to 17.0 mm. Width: 12.0 mm to 14.0 mm. Color: Upper surface: Light greenish-yellow (a color in between RHS 5B and RHS 6A); dotted (RHS 187B) and shaded (RHS 181B) at the base; white (RHS NN155C) toward whiskers. Lower surface: Dark red dots (RHS 187B) at the margin; light greenish-yellow (a color in between RHS 4C and RHS 4D) at the base; greenish-yellow (RHS 6A) toward wings; white (RHS NN155C) toward whiskers. Number of spots, dots, and stripes on the apical lobe: Very few dots. Color of spots, dots, and stripes on the apical lobe: RHS 187B. Density of netting of the apical lobe: None. Color of the netting: Not applicable. Bump and ridge: Present (small).

*Callus*.—Average size: Small. Height: 3.0 mm to 4.0 mm. Length: 3.0 mm to 4.0 mm. Width: 2.0 mm to 3.0 mm. Color: Dark red (RHS 187B) at the base and darker red (RHS 187A) toward the tip.

Reproductive organs:

*Column*.—Length: 7.0 mm to 9.0 mm. Diameter: 4.0 mm to 5.0 mm. Color: Dark red-purple (a color in between RHS 187A and RHS N79C) with white tip (RHS NN155C).

*Pollinia*.—Quantity: 2. Diameter: 0.6 mm to 0.8 mm. Color: Orange (RHS 24A).

*Ovary*.—Length: 11.0 mm to 13.0 mm. Diameter: 1.8 mm to 2.0 mm.

*Pedicel*.—Length: 30.0 mm to 32.0 mm. Diameter: 2.1 mm to 2.3 mm. Color: Dark purplish-red (RHS N79B) at the base; yellow-green (RHS 145B) and light yellow-green (RHS 145D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALIDDIK' differs from the female parent plant '01-4155' (unpatented) in that 'PHALIDDIK' has ovate apical lobes and very short whiskers, whereas '01-4155' has rhombic apical lobes and no whiskers.

'PHALIDDIK' differs from the male parent plant '01-3358' (unpatented) in that 'PHALIDDIK' has dark red-purple columns with white tips and small calluses, whereas '01-3358' has reddish-purple columns and medium calluses.

'PHALIDDIK' is most similar to the commercial *Phalaenopsis* plants named 'PHALGOPXO' (U.S. Plant Pat. No. 32,285) and 'PHALFUXE' (U.S. Plant Pat. No. 29,450). 'PHALIDDIK' differs from the commercial variety 'PHALGOPXO' in that 'PHALIDDIK' has rounded dorsal sepal apexes, dark red-purple columns with white tips, and ovate apical lobes, whereas 'PHALGOPXO' has obtuse dorsal sepal apexes, white columns, and rhombic apical lobes. Additionally, 'PHALIDDIK' has smaller flowers than 'PHALGOPXO'.

'PHALIDDIK' differs from the commercial variety 'PHALFUXE' in that 'PHALIDDIK' has ovate apical lobes, whereas 'PHALFUXE' has trullate apical lobes. Additionally, 'PHALIDDIK' has smaller flowers than 'PHALFUXE'.

I claim:

1. A new and distinct variety of *Phalaenopsis* plant named 'PHALIDDIK' substantially as described and illustrated herein.

* * * * *